(12) United States Patent
Suda (10) Patent No.: US 8,663,233 B2
(45) Date of Patent: Mar. 4, 2014

(54) BORING INSTRUMENT GUIDING DEVICE AND BORING ASSEMBLY

(75) Inventor: Kota Suda, Sapporo (JP)

(73) Assignees: Kota Suda, Hokkaido (JP); Kiehyun Daniel Riew, St. Louis, MO (US)

( * ) Notice: Subject to any disclaimer, the term of this patent is extended or adjusted under 35 U.S.C. 154(b) by 212 days.

(21) Appl. No.: 12/866,349

(22) PCT Filed: Dec. 25, 2008

(86) PCT No.: PCT/JP2008/073505
§ 371 (c)(1),
(2), (4) Date: Aug. 5, 2010

(87) PCT Pub. No.: WO2009/130824
PCT Pub. Date: Oct. 29, 2009

(65) Prior Publication Data
US 2010/0324560 A1    Dec. 23, 2010

(30) Foreign Application Priority Data
Apr. 23, 2008 (JP) ................................. 2008-112087

(51) Int. Cl.
*A61B 17/58* (2006.01)
*A61B 17/60* (2006.01)
*A61F 2/00* (2006.01)

(52) U.S. Cl.
USPC ............................................ 606/96; 606/104

(58) Field of Classification Search
USPC .......... 606/79, 86, 102, 86 R, 96–98, 87, 104
See application file for complete search history.

(56) References Cited

U.S. PATENT DOCUMENTS

| 4,860,735 A | 8/1989 | Davey et al. |
| 4,920,958 A * | 5/1990 | Walt et al. .................. 606/96 |
| 5,147,372 A | 9/1992 | Nymark et al. |

(Continued)

FOREIGN PATENT DOCUMENTS

| CN | 2680212 | 2/2005 |
| EP | 428452 A1 * | 5/1991 ............. A61B 17/16 |

(Continued)

OTHER PUBLICATIONS

International Search Report issued Mar. 10, 2009 in International (PCT) Application No. PCT/JP2008/073505.

(Continued)

*Primary Examiner* — Andrew Yang
*Assistant Examiner* — Diana S Jones
(74) *Attorney, Agent, or Firm* — Wenderoth, Lind & Ponack, L.L.P.

(57) ABSTRACT

A boring instrument guiding device which is used to guide a boring instrument that forms a pilot hole for embedding a pedicle screw in a vertebral pedicle includes a reference pin which is used as a reference by being inserted into the vertebral arch from the rear to the front of a spine, and an arm which extends sideward from the proximal end side of the reference pin, and is characterized in that a plurality of guide holes, each of which is opened toward the tip position of the reference pin to guide the boring instrument, are formed in the arm in a radial pattern centered at the tip position of the reference pin. It is possible to provide a boring instrument guiding device which is capable of more easily and precisely guiding the boring instrument.

10 Claims, 9 Drawing Sheets

(56) References Cited

U.S. PATENT DOCUMENTS

| | | | |
|---|---|---|---|
| 5,242,444 A * | 9/1993 | MacMillan | 606/86 R |
| 5,364,399 A | 11/1994 | Lowery et al. | |
| 5,423,826 A | 6/1995 | Coates et al. | |
| 5,968,050 A | 10/1999 | Torrie | |
| 6,187,011 B1 | 2/2001 | Torrie | |
| 7,927,333 B2 * | 4/2011 | Gradl | 606/86 B |
| 2003/0135211 A1 * | 7/2003 | Cho | 606/62 |
| 2003/0216742 A1 * | 11/2003 | Wetzler et al. | 606/96 |
| 2005/0177171 A1 | 8/2005 | Wetzler et al. | |
| 2006/0079908 A1 | 4/2006 | Lieberman | |
| 2006/0085010 A1 | 4/2006 | Lieberman | |
| 2006/0271059 A1 * | 11/2006 | Reay-Young et al. | 606/96 |
| 2007/0112351 A1 * | 5/2007 | Assell et al. | 606/61 |
| 2010/0145351 A1 * | 6/2010 | Ashman | 606/96 |

FOREIGN PATENT DOCUMENTS

| | | |
|---|---|---|
| JP | 2-142559 | 12/1990 |
| JP | 3-505985 | 12/1991 |
| JP | 9-504213 | 4/1997 |
| JP | 11-290337 | 10/1999 |
| JP | 2001-525210 | 12/2001 |
| JP | 2008-36248 | 2/2008 |
| WO | 95/11632 | 5/1995 |
| WO | 99/29237 | 6/1999 |
| WO | 2006/038959 | 4/2006 |

OTHER PUBLICATIONS

Supplementary European Search Report issued May 31, 2011 in corresponding European Application No. 08873992.5.

* cited by examiner

BORING INSTRUMENT GUIDING DEVICE AND BORING ASSEMBLY

This application is a National Stage application of International application PCT/W2008/073505, filed Dec. 25, 2008.

BACKGROUND OF THE INVENTION

I. Technical Field

The present invention relates to a boring instrument guiding device which, when a pilot hole for embedding a pedicle screw used for spinal fusion surgery as a spinal surgical operation is formed by a boring instrument, is used to precisely guide the insertion position and direction of the boring instrument, and relates to a boring assembly which forms the pilot hole.

II. Description of the Related Art

Figure 12:
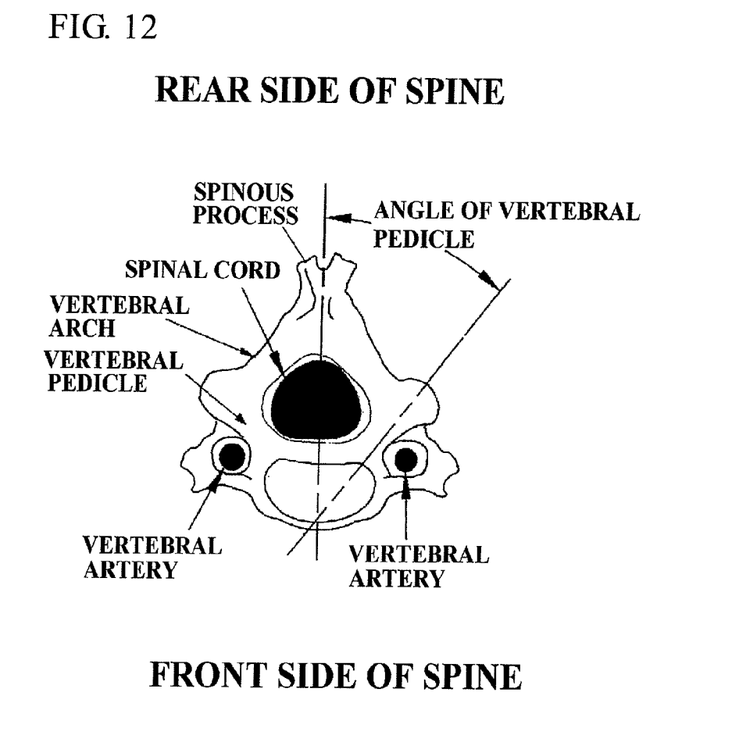
FIG. 12 is an axial cross section of a spine.
Figure 13:
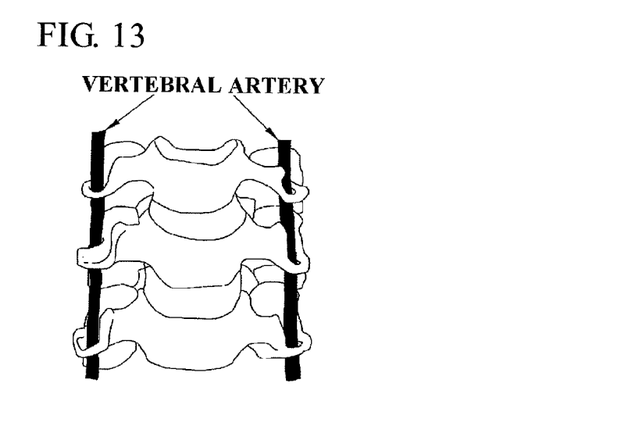
FIG. 13 is a view of the spine viewed from the front.
Figure 14:
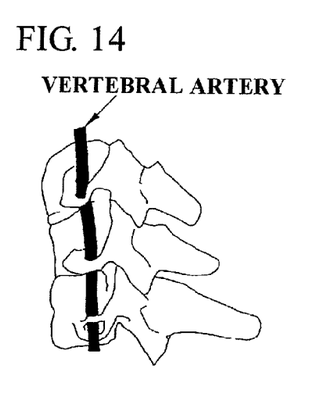
FIG. 14 is a view of the spine viewed from the side surface.

FIG. 12 is an axial cross-sectional view of a spine. FIG. 13 is a view of the spine viewed from the front thereof. FIG. 14 is a view of the spine viewed from the side thereof. The spinal fusion surgery is an excellent operation method for correcting and fixing the spine. In such a surgical operation of the spine, a method for embedding a pedicle screw in the spine is often used. The pedicle screw is embedded in such a manner that a pilot hole is formed beforehand by inserting a boring instrument, such as an awl and a tap, and that the pedicle screw is screwed into the pilot hole.

However, as shown in FIG. 12 to FIG. 14, in the vicinity of the spine, important organs, such as a spinal cord, a nerve root, a blood vessel, and an internal organ, are located close to each other. Thus, when the insertion position is incorrect, serious damage may occur in the organs. Therefore, it is necessary to precisely determine the insertion position.

Conventionally, the position of the pedicle into which the screw is to be inserted is checked from the front and side face images of the spine which are captured by an X-ray apparatus, and then an awl is inserted without a guide. However, there is a problem that a variation occurs in the operation result according to the operator's experience.

Thus, a navigation system of a pedicle probe is described in National Publication of International Patent Application No. 2008-36248. Specifically, the navigation system is a system which guides the insertion of the pedicle probe in spinal reconstruction surgery, and is characterized by a configuration that includes: an ultrasonic transducer for transmission and reception, which is provided at the distal end section of the pedicle probe; measurement means which, when the pedicle probe is inserted into the spongy bone of the vertebral pedicle, measures, by using the ultrasonic transducer, an ultrasonic echo signal generated at the boundary between the spongy bone and the cortical bone; analysis means which analyzes the waveform of the ultrasonic echo signal measured by the measurement means; and display means which displays, in real time, the result obtained by the measurement means, and/or the result obtained by the analysis means.

SUMMARY OF THE INVENTION

However, the device described in National Publication of International Patent Application No. 2008-36248 requires other devices, such as the ultrasonic transducer and a power source system for the ultrasonic transducer, and hence large-scale equipment is required. Further, the pedicle probe is made large in size due to the power source system for supplying power to the ultrasonic transducer.

In view of the above described problems, it is an object of the present invention to provide a boring instrument guiding device which is capable of guiding a boring instrument in a simpler manner.

To this end, a boring instrument guiding device according to the present invention, which is configured to guide a boring instrument that forms a pilot hole for embedding a pedicle screw in a vertebral pedicle, includes a reference pin that is used as a reference by being inserted into the base of the vertebral pedicle from the rear to the front of the spine, and an arm extending sideward from the proximal end side of the reference pin, and is characterized in that the reference pin has a length to allow the tip position thereof to reach the base of the vertebral pedicle, and in that a plurality of guide holes, each of which is opened toward the tip position of the reference pin to guide the boring instrument, are formed in the arm in a radial pattern centered at the tip position of the reference pin.

Thus, by making the boring instrument pass through the guide hole formed in the arm, it is possible to precisely guide the insertion angle of the boring instrument. Further, since the guide hole is opened toward the tip position of the reference pin, the insertion depth of the boring instrument can be precisely guided in such a manner that after the reference pin is inserted until the tip position thereof reaches an object point (target point) in the bone, the boring instrument is inserted until it is brought into contact with the tip position of the reference pin. In this way, the boring instrument guiding device according to the present invention has an excellent effect that not only the insertion angle of the boring instrument can be guided by the guide hole, but also, at the same time, the insertion depth of the boring instrument can be guided by the reference pin. Therefore, in the case where the insertion depth of the boring instrument is adjusted, it is not necessary to adjust the insertion depth while observing a monitor image, such as an X-ray radioscopic image.

Further, since the plurality of guide holes are formed so that each of the guide holes is radially shifted from the neighboring guide holes with the tip position of the reference pin as the center, the angle θ formed between the tip position of the reference pin and the extension line of the guide hole can be set in a plurality of stages. Therefore, the insertion angle of the boring instrument can be changed according to the inclination angle of the vertebral pedicle. That is, by selecting a guide hole having a suitable inclination angle θ, and by making the boring instrument pass through the selected guide hole, it is possible to precisely insert the boring instrument into the vertebral pedicle at the suitable inclination angle θ. In this way, according to the present invention, the insertion operation of the boring instrument can be precisely guided.

It is possible that a level difference is formed at a position in the longitudinal direction of the reference pin, that a small diameter section is formed from the level difference to the tip of the reference pin, and that a large diameter section is formed from the level difference to the proximal end of the reference pin. When the reference pin is inserted from the rear side of the spine to the base of the vertebral pedicle, the level difference serves as a stopper so as to be caught by the surface of the vertebral arch, and hence the insertion depth can be fixed. The small diameter section has the same length as the target insertion depth Y.

The reference pin can be configured to be freely attached and detached to and from the arm. The reference pin can be exchanged for the other suitable reference pin. Further, it is possible to adopt a use method in which after only the reference pin is inserted into the base of the vertebral pedicle, the reference pin is attached to the arm.

Further, it is possible that a plurality of reference pins, each of which has the small diameter section having a different longitudinal length, are prepared so as to be capable of being exchanged for each other. The reference pin having a suitable small diameter section can be selected according to the target insertion depth, and the insertion depth of the reference pin can be changed.

It is possible to provide a caliper which is configured by a connecting body that is fixed to the proximal end side of the reference pin and that extends in the direction opposite to the extending direction of the arm, and a caliper pin that is supported by the connecting body so as to be in parallel to the reference pin. When the reference pin and the caliper pin are brought into contact with the vertebral arch so that the spinous process is straddled from the rear side of the spine, it is possible to prevent the reference pin from being inclined sideward. Thereby, the positioning of the reference pin can be precisely performed, and the insertion position of the boring instrument can be precisely set.

The reference pin and the caliper pin can be moved in the direction approaching and separating from each other. In this case, the caliper pin may be supported by the connecting body so as to be able to be moved for adjustment in a direction approaching and separating from the reference pin. On the contrary, the reference pin may be supported by the connecting body so as to be capable of being moved for adjustment in a direction approaching and separating from the caliper pin. Further, both the configurations may also be adopted. When the reference pin and the caliper pin are brought into contact with the vertebral arch so that the angular-shaped spinous process is straddled, the reference pin and the caliper pin are disposed at left and right symmetrical positions, and hence the middle position of the reference pin and the caliper pin becomes the central position of the vertebral canal. Therefore, when the width between the reference pin and the caliper pin is set as X, there is a relationship that one-half the width X is the width between the central position of the vertebral canal and the insertion position. Thus, the width between the central position of the vertebral canal and the insertion position can be changed by adjusting the distance between the reference pin and the caliper pin.

The connecting body can support the caliper pin so that the caliper pin can be moved in the longitudinal direction thereof. In the case where, after the insertion position of the reference pin is determined by bringing the reference pin and the caliper pin into contact with the vertebral arch as described above, the reference pin is inserted into the base of the vertebral pedicle, since the caliper pin can be moved in the longitudinal direction thereof with respect to the connecting body, only the necessary reference pin can be inserted into the base of the vertebral pedicle.

Further, the present invention provides the boring instrument guiding device described above, and a boring assembly provided with a boring instrument which can be detachably inserted into the guide hole. A pilot hole for embedding a pedicle screw can be formed at a precise position in such a manner that the boring instrument guiding device is set at the vertebral arch, and that the boring instrument is made to pass through the guide hole so as to be inserted into the vertebral pedicle. Note that an instrument, such as an awl and a tap, which has a boring function, can be used as the boring instrument.

The boring instrument guiding device and the boring assembly according to the present invention are used to embed a pedicle screw in the vertebral pedicle of each of the cervical vertebrae. Thus, it is possible to fix the spine by a method, such as a method of bridging between each pair of the neighboring pedicle screws by a rod or a frame. The boring instrument guiding device and the boring assembly, according to the present invention, are suitably applied to the cervical vertebrae in the spinal fusion surgery, but can also be applied to the other spine portions, such as the lumbar vertebrae and the thoracic vertebrae. The boring instrument guiding device and the boring assembly according to the present invention can be particularly suitably applied to the third to seventh cervical vertebrae among the cervical vertebrae consisting of the seven vertebrae (the first cervical vertebra to the seventh cervical vertebra). Note that the boring instrument guiding device and the boring assembly according to the present invention are different from the device used in the Magerl method (atlantoaxial transarticular screw fixation method) for treating instability of the upper cervical vertebrae, that is, the atlantoaxial instability. The Magerl method is a fixing method in which the joint of the first cervical vertebra (atlas) and the second cervical vertebra (axis) is locked in such a manner that a screw is inserted into the joint so as to skewer the joint. Thus, the Magerl method is different from the boring instrument guiding device according to the present invention which is used to embed a pedicle screw in each vertebral pedicle.

According to the present invention, the insertion angle of the boring instrument can be precisely guided by making the boring instrument pass through the guide hole formed in the arm. Further, the guide hole is opened toward the tip position of the reference pin. Thus, when the boring instrument is inserted until it is brought into contact with the tip position of the reference pin, the insertion depth can be precisely guided.

Further, the plurality of guide holes are formed so that each of the guide holes is radially shifted from the neighboring guide holes with the tip position of the reference pin as the center. Thus, by selecting a guide hole having a suitable angle, it is possible to precisely insert the boring instrument into the vertebral pedicle at the suitable inclination angle θ. In this way, according to the present invention, the insertion operation of the boring instrument can be precisely guided.

BRIEF DESCRIPTION OF THE DRAWINGS

FIG. 5(a) is a view showing a state in which a reference pin is inserted;

FIG. 5(b) is a view showing a state in which a boring instrument is inserted;

FIG. 11(*a*) is a view showing a state in which the boring instrument guiding device is brought into contact with the vertebral arch;

FIG. 11(*b*) is a view showing a state in which the reference pin is inserted;

FIG. 11(*c*) is a view showing a state in which the boring instrument is inserted;

DETAILED DESCRIPTION OF THE INVENTION

In the following, embodiments according to the present invention will be described with reference to the accompanying drawings.

First Embodiment

Figure 1:
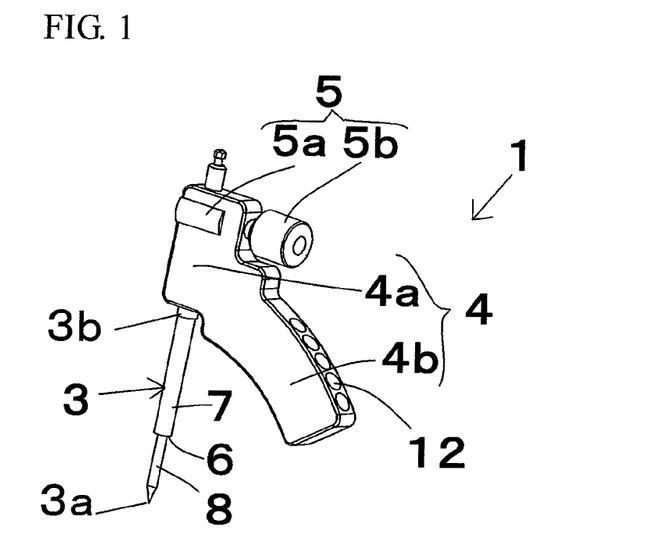
FIG. 1 is a perspective view of a boring instrument guiding device according to a first embodiment.
Figure 2:
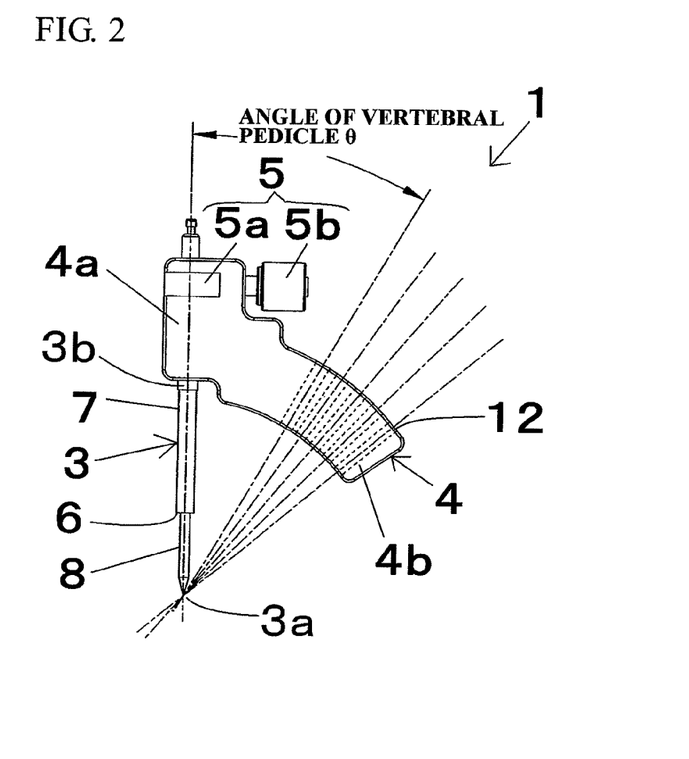
FIG. 2 is a front view of the boring instrument guiding device according to the first embodiment.
Figure 3:
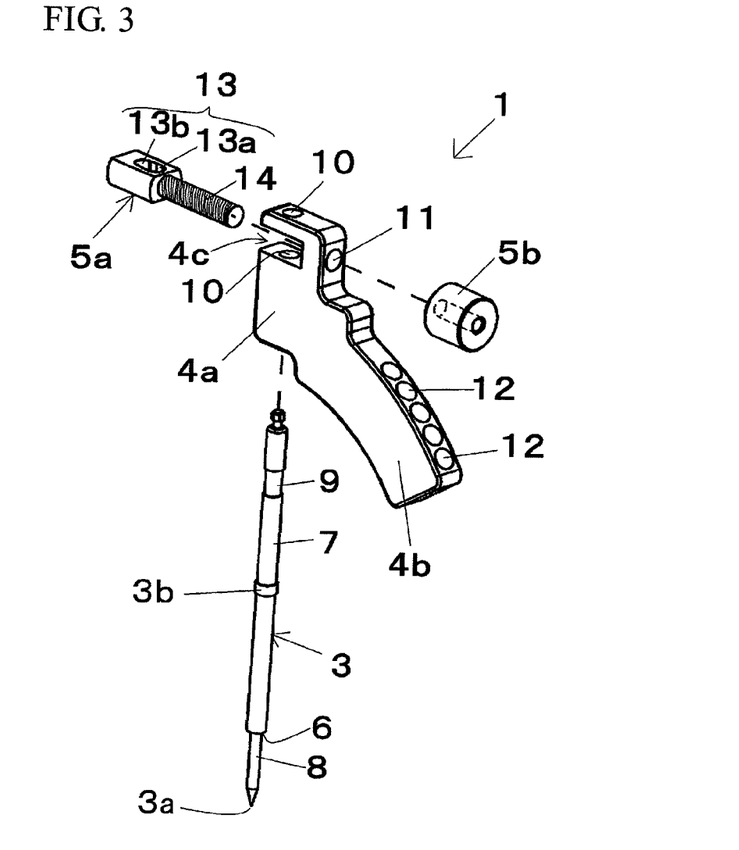
FIG. 3 is an exploded perspective view of the boring instrument guiding device according to the first embodiment.
Figure 4:
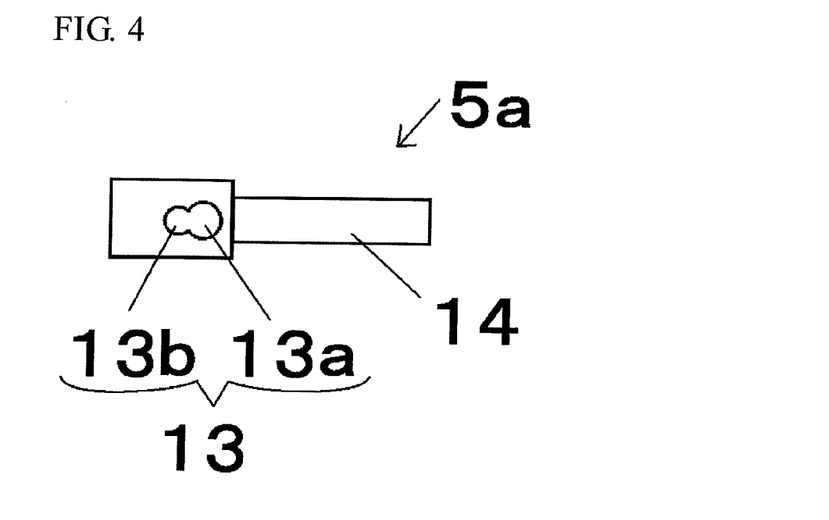
FIG. 4 is a plan view of a first fixing body.
Figure 5:
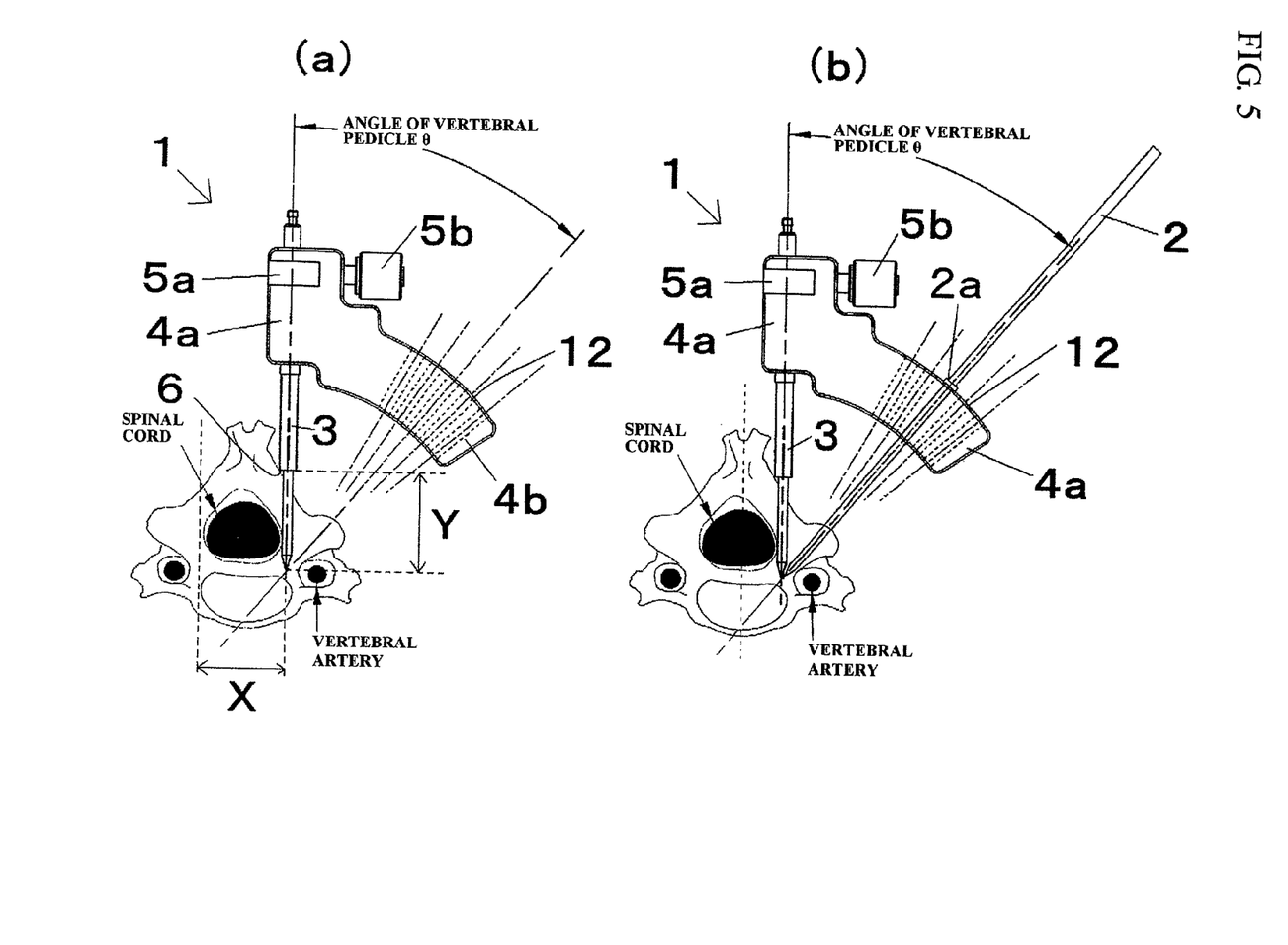
FIG. 5 is a view showing a use state of the boring instrument guiding device according to the first embodiment.
Figure 6:
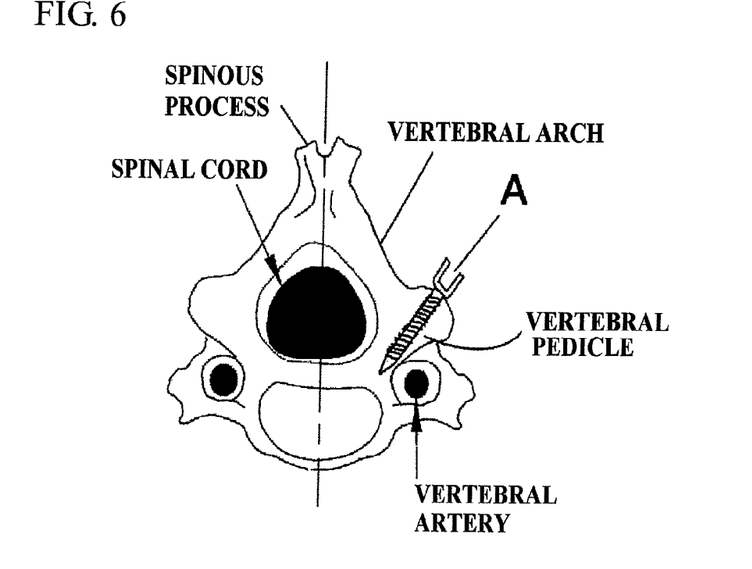
FIG. 6 is a view showing a state in which a pedicle screw is embedded.
Figure 7:
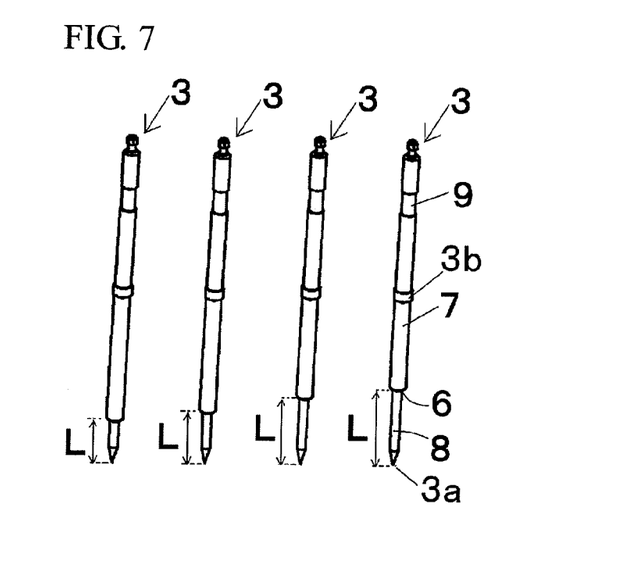
FIG. 7 is a view showing a variation of the reference pin.

FIG. 1 is a perspective view of a boring instrument guiding device according to a first embodiment. FIG. 2 is a front view of the boring instrument guiding device according to the first embodiment. FIG. 3 is an exploded perspective view of the boring instrument guiding device according to the first embodiment. FIG. 4 is a plan view of a first fixing body. FIG. 5 is a view showing a use state of the boring instrument guiding device according to the first embodiment. FIG. 5(*a*) is a view showing a state in which a reference pin is inserted. FIG. 5(*b*) is a view showing a state in which a boring instrument is inserted. FIG. 6 is a view showing a state in which a pedicle screw is embedded. FIG. 7 is a view showing a variation of the reference pin.

A boring instrument guiding device 1 according to the present embodiment is a device for guiding a boring instrument 2 which forms a pilot hole for embedding a pedicle screw in a vertebral pedicle. A boring assembly is configured by combining the boring instrument guiding device 1 with the boring instrument 2.

As shown in FIG. 1 to FIG. 3, the boring instrument guiding device 1 is configured by a reference pin 3 which is used as a reference by being inserted into the base of the vertebral pedicle from the rear to the front of a spine, an arm 4 which allows the reference pin 3 to pass therethrough and which extends sideward from the proximal end side of the reference pin 3, and a fixing means or device 5 which fixes the longitudinal movement of the reference pin 3 with respect to the arm 4. In this way, the arm 4 detachably supports the reference pin 3 by means of the fixing means 5.

The material of the reference pin 3 is not limited in particular, but the reference pin 3 may be made of stainless steel. The reference pin 3, which has a pointed tip, is positioned in such a manner that it is brought into contact with the vertebral arch from the rear of the spine so as to be inserted to reach the base of the vertebral pedicle. The reference pin 3 has a length to allow the tip position 3*a* thereof to reach the base of the vertebral pedicle. Further, the reference pin 3 has a level difference 6 (i.e., step) in the middle thereof in the longitudinal direction. The diameter on the tip side is set smaller than the diameter on the proximal end side (hand side) so that the portion on the proximal end side from the level difference 6 is formed as a large diameter section 7, and so that the portion on the tip side from the level difference 6 is formed as a small diameter section 8. The level difference 6 plays a role of a stopper at the time of insertion of the reference pin 3. Thereby, the insertion depth of the reference pin 3 can be fixed. Note that the diameter of the small diameter section 8 (except the tip) of the reference pin 3 is set to 2 mm, and the diameter of the large diameter section 7 set to 3.5 mm. However, the diameter of these sections is not limited to these values.

Further, a plurality of the reference pins 3, in which the longitudinal length L of the small diameter section 7 is changed as shown in FIG. 7, are prepared. The length L of the small diameter section 7 becomes longer toward the right side in FIG. 7. Specifically, the reference pins 3, in which the longitudinal length L of the small diameter section 7 is changed at a pitch of 2 mm within a range of 10 mm to 18 mm, are prepared. However, the length of the small diameter section 7 of the reference pins 3 is not limited thereto. When the plurality of reference pins 3, in which the length L of the small diameter section 7 is changed in this way, are prepared, the insertion depth of the reference pin 3 can be precisely set by exchanging the reference pin 3 for one having the small diameter section 7 whose length is the same as the target insertion depth Y.

Further, a groove 9 is also peripherally formed in the large diameter section 7 of the reference pin 3. The groove 9 serves to position the reference pin 3 in the longitudinal direction thereof at the time when the reference pin 3 is fixed to the arm 4. Further, a projecting section 3*b* is provided on the tip side of the reference pin 3 from the groove 9. The projecting section 3*b* also serves to position the reference pin 3 in the longitudinal direction thereof in such a manner that the proximal end side of the projecting section 3*b* is brought into contact with a base 4*a* of the arm 4.

The material of the arm 4 is not limited in particular, but the arm 4 may be made of stainless steel. The arm is configured by the base 4*a* in which a through hole 10 is formed to allow the reference pin 3 to vertically pass therethrough, and an extension 4*b* which is extended so that a circular arc centered at the tip position 3*a* of the reference pin 3 is formed from the lower side end of the base 4*a* to the sideward direction. Note that the extension 4*b* may not be formed in the circular arc shape, but may be extended so as to be formed in a linear shape. Further, the arm 4 may be made of another material, such as aluminum and X-ray transmitting resin. Further, the base 4*a* has a cutout section 4*c* which is formed by cutting out a part of the base 4*a* so as to expose the middle of the through hole 10, and a fixing hole 11 is formed in the side wall of the cutout section 4*c*.

A guide hole 12, which is opened toward the tip position of the reference pin 3, is formed in the extension 4*b*. The guide hole 12 guides the insertion direction of the boring instrument 2. It is preferred that the size of the guide hole 12 is set approximately equal to the diameter of the boring instruments 2, such as an awl, so as to enable the boring instrument 2 to pass through the guide hole 12. Further, the shape of the guide hole 12 is formed into a circular shape, but may be changed according to the cross-sectional shape of the boring instrument 2. Further, the guide hole 12 needs to have at least a length to be able to support the insertion direction of the boring instrument 2.

Further, a plurality of the guide holes 12 are formed so that each of the guide holes 12 is radially shifted from the neighboring guide holes 12 with the tip position 3*a* of the reference pin 3 as the center. Thus, the angle θ formed between the tip position 3*a* of the reference pin 3 and the extension line of the guide hole 12 can be set in a plurality of stages. Therefore, the insertion angle of the boring instrument 2 can be changed in a plurality of stages. Specifically, the five guide holes 12 are formed at a 5 degree pitch within a range of 30 degrees to 50 degrees. However, the number of the guide holes 12, and the range of the angle are not limited to these. When one of the guide holes 12, which has a suitable inclination angle θ, is selected, and when the boring instrument 2 is made to pass through the selected guide hole 12, the boring instrument 2 can be precisely inserted into the vertebral pedicle at the suitable inclination angle θ.

The fixing means 5 is configured by a first fixing body 5a which has a through hole 13, and a second fixing body 5b which is adapted to mate with the first fixing body 5a. As shown in FIG. 4, the through hole 13 is formed such that a large hole 13a having a diameter approximately equal to the diameter of the large diameter section 7 of the reference pin 3 and a small hole 13b having a diameter approximately equal to the diameter of the groove 9 are adjacent and connected to each other. A pin 14 extended from the large hole 13a side of the first fixing body 5a is made to pass through the fixing hole 11 formed in the side wall of the cutout section 4c of the arm 4, so that the first fixing body 5a is fitted into the cutout section 4c. In the state where the large hole 13a of the through hole 13 and the through hole 10 of the arm 4 are aligned with each other, the reference pin 3 is made to pass through each of the holes 13a and 10. The large diameter section 7 can pass through the inside of the large hole 13a. Then, the position adjustment is performed so that the position of the groove 9 of the reference pin 3 is positioned at the large hole 13a. Thereafter, the second fixing body 5b is screwed and fastened to the pin 14 of the first fixing body 5a. Along with the screwing operation, the first fixing body 5a is moved to the fixing hole 11 side, and the small hole 13b of the first fixing body 5a is moved to the position coincident with the through hole 10 of the arm 4. Thus, the portion of the groove 9 of the reference pin 3 is shifted to the small hole 13b side. The large diameter section 7 cannot pass through the small hole 13b, and hence the longitudinal movement of the reference pin 3 can be fixed. In this way, the arm 4 can detachably support the reference pin 3 by the screwing operation of the second fixing body 5b.

An instrument, such as an awl and a tap, which has a boring function, is used as the boring instrument 2. The boring instrument 2 has a pointed tip and can be inserted into the vertebral pedicle. A projecting stopper 2a is provided in the middle of the boring instrument 2. The boring instrument 2 is configured such that the stopper 2a is brought into contact with the upper surface of the extension 4b of the arm 4 at the time of insertion of the boring instrument 2 so that the boring instrument 2 is stopped at the position where the tip end of the boring instrument 2 is brought into contact with the tip position 3a of the reference pin 3.

A case where spinal fusion surgery is performed through the posterior surgical exposure by using the boring instrument guiding device 1 configured as described above will be specifically described. First, on the basis of a CT (Computed Tomography) tomogram, a width X (of the base of the vertebral pedicle) between left and right insertion positions, a depth Y to the insertion position in the perpendicular direction (the front and rear direction of the body), and an angle θ of the vertebral pedicle are measured.

Next, a mark is formed at each of the positions across the width X on the spine surface. Then, the reference pin 3, which has the small diameter section 8 having the same length as the depth Y to the insertion position in the perpendicular direction, is selected. The selected reference pin 3 is fixed to the arm 4 by using the fixing means 5. The tip of the reference pin 3 is brought into contact with the mark, and the reference pin 3 is inserted in the perpendicular direction until it is stopped by the level difference 6, as shown in FIG. 5(a). In this manner, the insertion depth of the reference pin 3 can be fixed.

Then, as shown in FIG. 5(b), the boring instrument 2, such as an awl, is inserted into the guide hole 12 having the same inclination angle θ as the angle θ of the vertebral pedicle, until the boring instrument 2 is brought into contact with the tip position 3a of the reference pin 3. Thereby, it is possible to precisely guide the insertion angle and the insertion depth of the boring instrument 2.

Thereafter, when the boring instrument 2 and the reference pin 3 are extracted, the process for forming the pilot hole for embedding a pedicle screw is completed. Then, as shown in FIG. 6, the pedicle screw A can be screwed into the pilot hole.

In this way, the guide hole 12 formed in the arm 4 is opened toward the tip position 3a of the reference pin 3. Thus, when the boring instrument 2 is made to pass through the guide hole 12 and is inserted until it is brought into contact with the tip position 3a of the reference pin 3, the insertion angle and the insertion depth of the boring instrument can be precisely guided. Further, one of the guide holes 12, which has a suitable inclination angle θ, can be selected, and hence the boring instrument 2 can be precisely inserted into the vertebral pedicle at the suitable inclination angle. In this way, according to the present invention, the insertion operation of the boring instrument can be precisely guided.

Note that in the above described embodiment, after the reference pin 3 and the arm 4 are assembled, the insertion operation of the reference pin 3 is performed. However, it may also be configured such that the reference pin 3 is independently inserted beforehand into the base of the vertebral pedicle, and such that in the state where the reference pin 3 is inserted, the reference pin 3 is then fixed to the arm 4 and the boring instrument 2 is inserted.

Second Embodiment

Figure 8:
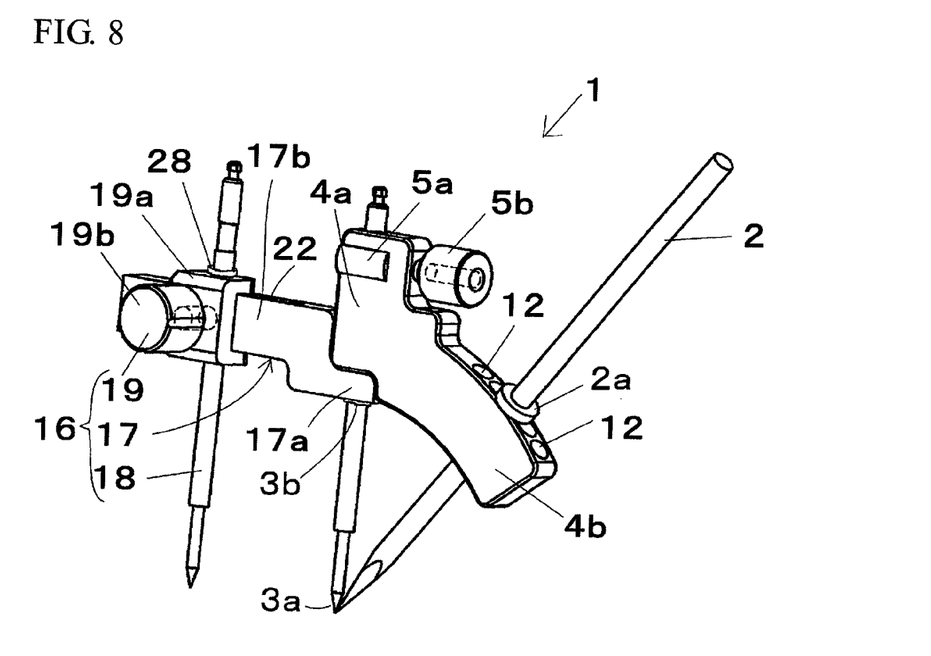
FIG. 8 is a perspective view of a boring assembly according to a second embodiment.
Figure 9:
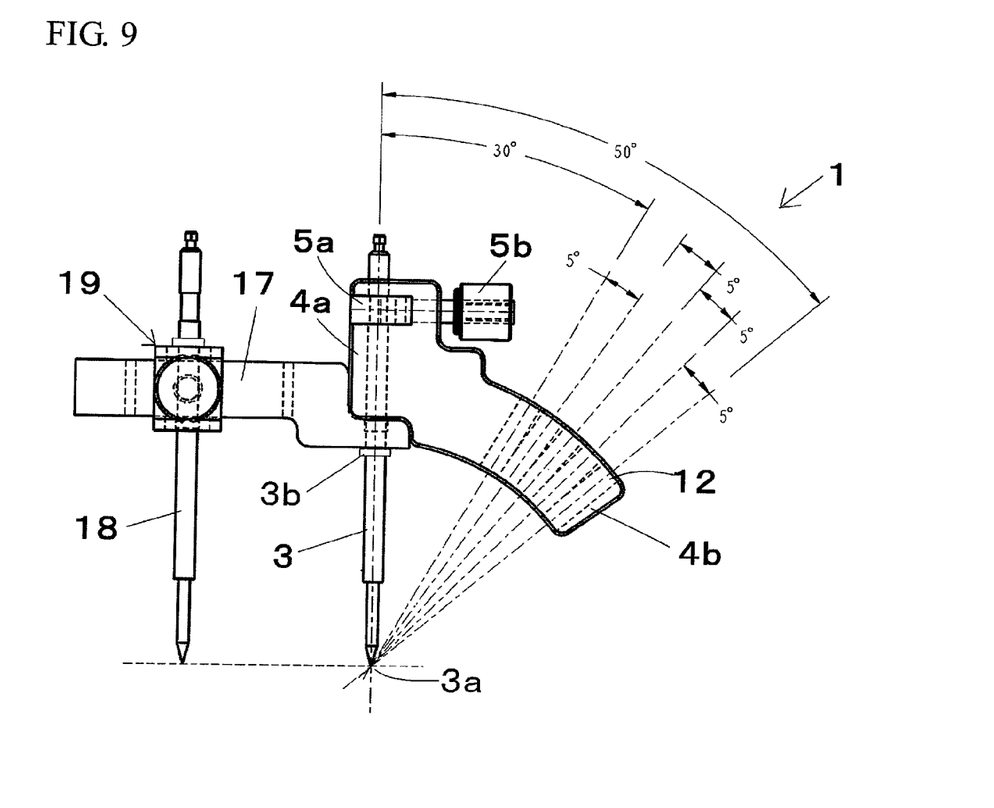
FIG. 9 is a front view of the boring instrument guiding device according to the second embodiment.
Figure 10:
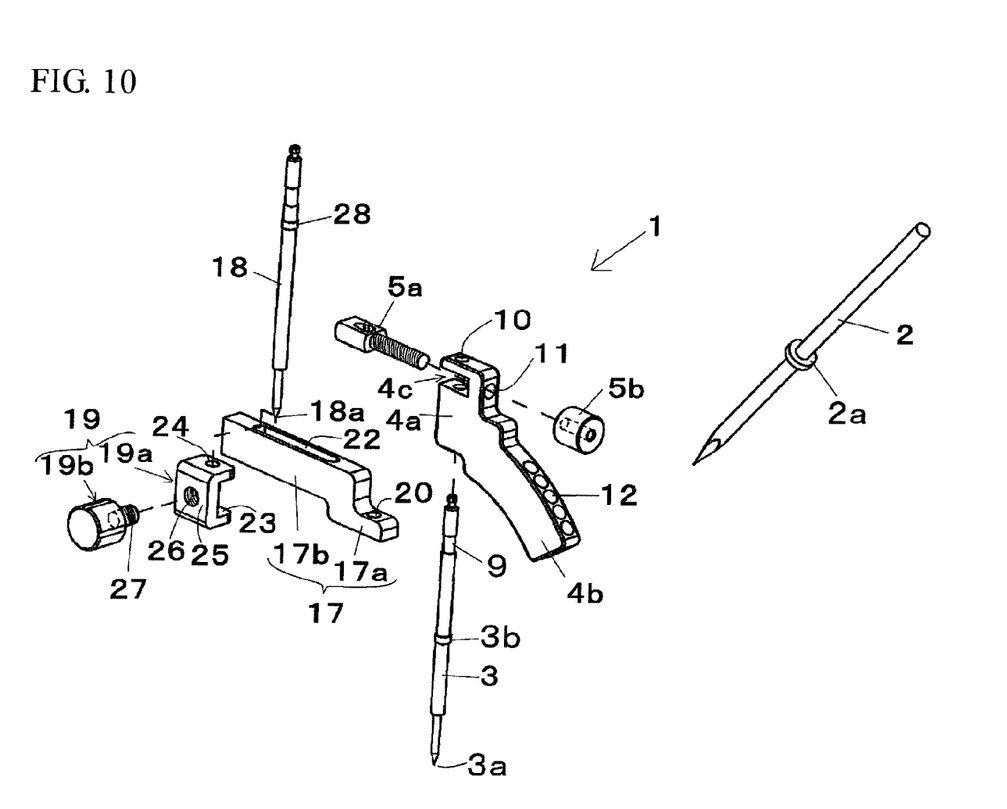
FIG. 10 is an exploded perspective view of the boring assembly according to the second embodiment.
Figure 11:
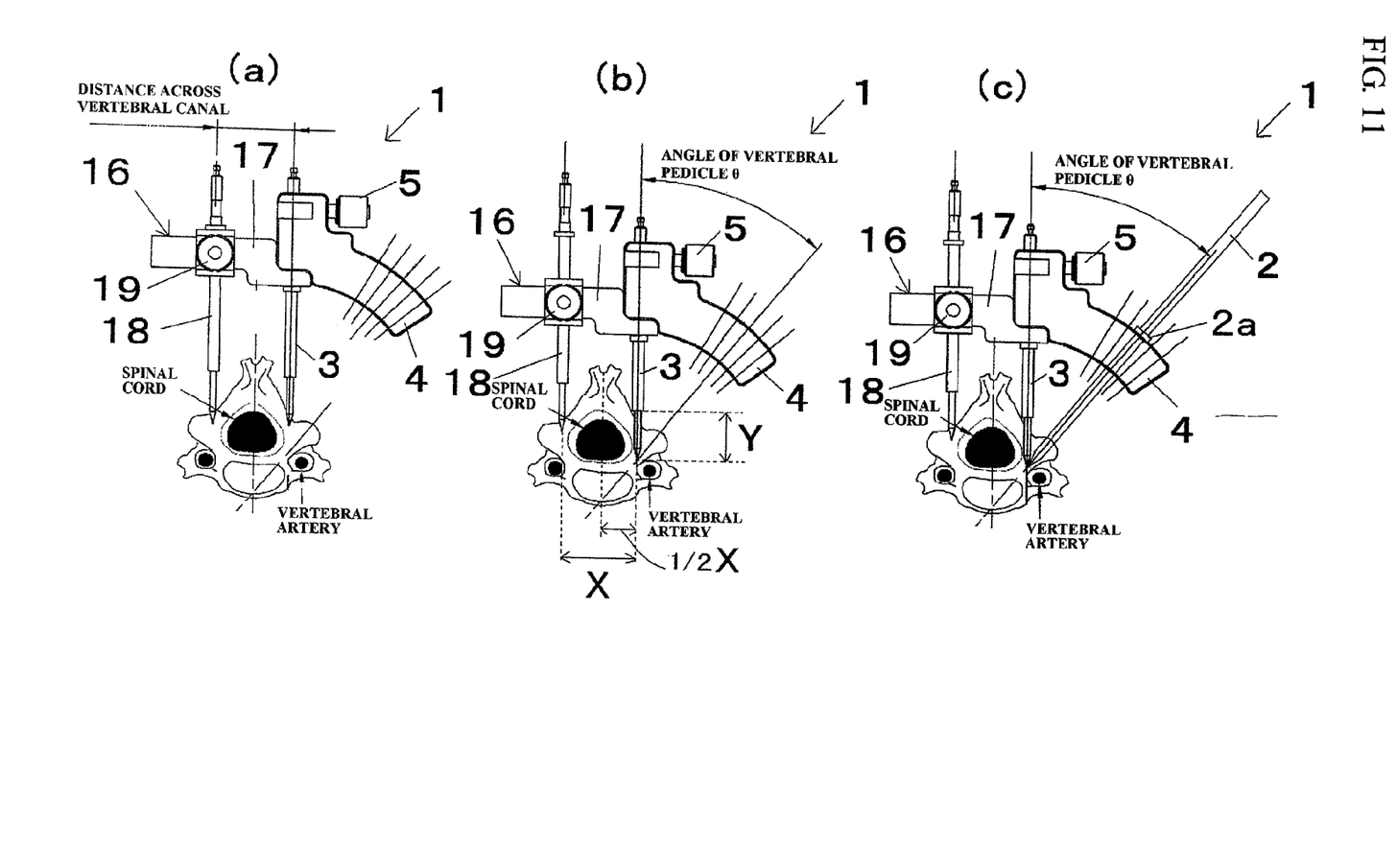
FIG. 11 is a view showing a use state of the boring instrument guiding device according to the second embodiment.

FIG. 8 is a perspective view of a boring assembly according to a second embodiment. FIG. 9 is a front view of the boring instrument guiding device according to the second embodiment. FIG. 10 is an exploded perspective view of the boring assembly according to the second embodiment. FIG. 11 is a view showing a use state of the boring instrument guiding device according to the second embodiment. FIG. 11(a) is a view showing a state in which the boring instrument guiding device is brought into contact with the vertebral arch. FIG. 11(b) is a view showing a state in which the reference pin is inserted. FIG. 11(c) is a view showing a state in which the boring instrument is inserted.

As shown in FIG. 8 to FIG. 11, in a boring instrument guiding device 1 according to the present embodiment, a caliper 16 is provided in addition to the configuration of the first embodiment. The other fundamental configurations of the present embodiment are the same as those of the above described first embodiment. Thus, since the effect of each of the fundamental configurations according to the present embodiment is the same as that of the first embodiment, the detailed description thereof is omitted, and the caliper 16 unique to the present embodiment will be briefly described.

As shown in FIG. 8 to FIG. 10, the boring instrument guiding device 1 according to the present embodiment is configured by the reference pin 3 which is used as a reference by being brought into contact with the vertebral arch and being inserted to reach the base of the vertebral pedicle in the direction from the rear to the front of the spine, the arm 4 which makes the reference pin 3 pass therethrough and which extends sideward, the fixing means 5 which fixes the movement of the reference pin 3 in the longitudinal direction thereof with respect to the arm 4, and the caliper 16.

The caliper 16 is configured by a connecting body 17 which is fixed to the large diameter section 7 of the reference pin 3 and which extends in the direction opposite to the extending direction of the arm 4, a caliper pin 18 which is supported by the connecting body 17 so as to be in parallel to the reference pin 3, and a caliper pin fixing means or device 19 which fixes the movement of the caliper pin in the side direction (the extending direction of the connecting body 17) with respect to the connecting body 17.

Although the material of the connecting body 17 is not limited, the connecting body 17 is made of stainless steel, and is configured by a connecting body base 17a, in which a first insertion hole 20 that allows the reference pin 3 vertically pass therethrough is formed, and a connecting body extension 17b which is extended sideward from the connecting body base 17a. The connecting body 17 is fixed so as to be arranged on the straight line of the arm 4 with respect to the reference pin 3. Note that the connecting body 17 may be formed of another material, such as aluminum and X-ray transmitting resin.

The connecting body base 17a is detachably fixed to the reference pin 3 in such a manner that the reference pin 3 is inserted into the first insertion hole 20 so as to make the connecting body base 17a sandwiched between the proximal end side surface of the projecting section 3b projectingly formed in the middle of the large diameter section 7 of the reference pin 3 and the base 4a of the arm 4.

The connecting body extension 17b has a second insertion hole 22 through which the caliper pin 18 is inserted, and the second insertion hole 22 is formed to be long in the extending direction. In this way, the second insertion hole 22 is formed in a slot shape, and hence the caliper pin 18 can be freely moved in the extending direction.

The caliper pin fixing means 19 is configured by a first caliper pin fixing body 19a formed in a U-shape, and a second caliper pin fixing body 19b. The first caliper pin fixing body 19a has two mutually facing wall surfaces 23, in each of which a caliper pin through hole 24 that allows the caliper pin 18 to pass therethrough is formed. The first caliper pin fixing body 19a is attached so that both sides of the second insertion hole 22 of the connecting body extension 17b are sandwiched between the two wall surfaces 23 of the first caliper pin fixing body 19a. The caliper pin 18 is inserted from above so as to pass through the two caliper pin through holes 24 of the first caliper pin fixing body 19a and the second insertion hole 22 of the connecting body extension 17b. Further, a stop hole 26 is formed in a connecting wall 25 which connects between the mutually facing wall surfaces 23 of the first caliper pin fixing body 19a. A groove is formed on the inner surface of the stop hole 26. The movement of the first caliper pin fixing body 19a in the extending direction of the connecting body extension 17b can be fixed in such a manner that the thread section 27 of the second caliper pin fixing body 19b is fastened by being screwed into the stop hole 26, and that the distal end of the thread section 27 is made to press against the wall surface of the connecting body extension 17b. The position of the caliper pin 18 in the extending direction can be adjusted by adjusting the fixed position of the first caliper pin fixing body 19a with respect to the connecting body extension 17b. That is, the caliper pin 18 is supported by the connecting body 17 so as to be able to be moved for adjustment in a direction approaching and separating from the reference pin 3.

Note that the fixing method using the caliper fixing means 19 is not limited to the above described method as long as the fixing method enables the caliper pin 18 to be moved for adjustment in a direction approaching and separating from the reference pin 3. For example, instead of the hole having the slot shape, a plurality of holes may be formed as the second insertion hole 22 of the connecting body extension 17b. The distance between the caliper pin 18 and the reference pin 3 may be adjusted by making the caliper pin 18 pass through the second insertion hole 22 formed at a suitable position.

A peripherally projected projecting section 28 is formed on the caliper pin 18. The projecting section 28 serves as a stopper by being brought into contact with the wall surface 23 of the first caliper pin fixing body 19a, and can prevent the caliper pin 18 from being moved in the direction of the tip thereof with respect to the connecting body extension 17b. On the contrary, the caliper pin 18 is freely movable in the proximal end direction thereof.

Further, it is set such that the height of the tip position 3a of the reference pin 3 is equal to the height of the tip position 18a of the caliper pin 18. According to the above described configuration, when the reference pin 3 and the caliper pin 18 are brought into contact with the vertebral arch so that the angular-shaped spinous process is straddled, the reference pin and the caliper pin are disposed at left and right symmetrical positions so that the middle position between the reference pin 3 and the caliper pin 18 corresponds to the central position of the vertebral canal. Therefore, when the width between the reference pin 3 and the caliper pin 18 is set as X, there is a relationship that one-half the width X is equal to the width between the central position of the vertebral canal and the insertion position. Thus, the width between the central position of the vertebral canal and the insertion position can be changed by adjusting the distance between the reference pin 3 and the caliper pin 18.

A case where spinal fusion surgery is performed through the posterior surgical exposure by using the boring instrument guiding device 1 configured as described above will be specifically described. First, by using a CT (Computed Tomography) tomogram, a width X (of the base of the vertebral pedicle) between left and right insertion positions, a depth Y to the insertion position in the perpendicular direction (the front and rear direction of the body), and an angle θ of the vertebral pedicle are measured.

One of the reference pins 3, which has the small diameter section 8 having the same length as the depth Y to the insertion position in the perpendicular direction, is selected. The selected reference pin 3 is made to pass through the through hole 10 of the arm 4 and the first insertion hole 20 of the connecting body 17 from below, and is fixed to the arm 4 by using the fixing means 5. Further, the position of the caliper pin 18 in the extending direction is adjusted and fixed by the caliper pin fixing means 19 so that the distance between the reference pin 3 and the caliper pin 18 becomes equal to the width X (of the base of the vertebral pedicle) between the left and right insertion positions. Then, as shown in FIG. 11(a), the reference pin 3 and the caliper pin 18 are brought into contact with the angular-shaped vertebral arch so that the spinous process is straddled. Since the angular shape of the vertebral arch is left-right symmetric, when the reference pin 3 and the caliper pin 18, which have the same height of the tip position, are brought into contact with the vertebral arch, it is possible to place the reference pin 3 at the insertion position.

Then, as shown in FIG. 11(b), the reference pin 3 is perpendicularly inserted until it is stopped by the level difference 6. At this time, the caliper pin 18 can be freely moved in the proximal end direction thereof with respect to the connecting body extension 17b, and hence the caliper pin 18 is not deeply inserted into the vertebral arch.

Next, as shown in FIG. 11(c), the boring instrument 2, such as an awl, is made to pass through the guide hole 12 having the same inclination angle θ as the angle θ of the vertebral pedicle, and is inserted into the vertebral pedicle until it is brought into contact with the tip position 3a of the reference pin 3. Thereafter, when the boring instrument 2 and the reference pin 3 are extracted, the process for forming the pilot hole for embedding a pedicle screw is completed. The pedicle screw A can be screwed into the pilot hole.

In this way, by adjusting the interval between the reference pin 3 and the caliper pin 18, the reference pin 3 can be more precisely positioned.

INDUSTRIAL APPLICABILITY

The present invention is to provide a boring instrument guiding device capable of more easily and precisely guiding a boring instrument, and has industrial applicability.

The invention claimed is:

1. A boring instrument guiding device which is configured to guide a boring instrument that forms a pilot hole for embedding a pedicle screw in a vertebral pedicle of the third cervical vertebra to the seventh cervical vertebra, said device comprising:
   a reference pin having a tip position and a proximal end side, and being configured to be used as a reference by being inserted into a base of the vertebral pedicle from a rear to a front of a spine; and
   an arm extending sideward from said proximal end side of said reference pin,
   wherein said reference pin has a length that enables said tip position of said reference pin to reach the base of the vertebral pedicle, and is completely straight,
   wherein said reference pin includes a step portion, said step portion being defined, in the longitudinal direction of said reference pin, by a diameter difference between a large diameter section of said reference pin and a small diameter section of said reference pin, said large diameter section extending from said step portion to said proximal end of said reference pin, said small diameter section extending from said step portion to said tip of said reference pin and having the same length as a target insertion depth, and said step portion being configured and arranged so as to be capable of being a stopper that engages the surface of the vertebral arch, and
   wherein said arm includes a plurality of guide holes, each guide hole of said plurality of guide holes being opened toward said tip position of said reference pin to guide said boring instrument, said plurality of guide holes being disposed in said arm in a radial pattern centered at said tip position of said reference pin.

2. The boring instrument guiding device according to claim 1, wherein said reference pin is detachably supported by said arm.

3. The boring instrument guiding device according to claim 1, wherein said reference pin is one of a plurality of reference pins, and each small diameter section of each reference pin has a different longitudinal length than each other small diameter of each other reference pin, and each said reference pin of said plurality of reference pins is configured so as to be exchangeable for each other said reference pin of said plurality of reference pins.

4. The boring instrument guiding device according to claim 1, further comprising a caliper including a connecting body fixed to said reference pin and extending in the direction opposite to the extending direction of said arm, and a caliper pin supported by said connecting body so as to be parallel to said reference pin.

5. The boring instrument guiding device according to claim 4, wherein said reference pin and said caliper pin are capable of being moved in a direction approaching and separating from each other.

6. The boring instrument guiding device according to claim 5, wherein said caliper pin is supported by said connecting body so as to be capable of being moved for adjustment in a direction approaching and separating from the reference pin.

7. The boring instrument guiding device according to claim 4, wherein said caliper pin is supported by said connecting body so as to be movable in the longitudinal direction.

8. A boring assembly comprising:
   said boring instrument guiding device according to claim 1; and
   a boring instrument capable of being detachably inserted into at least one guide hole of said plurality of guide holes.

9. The boring assembly according to claim 8, wherein said boring device includes a stopper configured and arranged so as to stop said boring instrument at a position in which a tip of said boring instrument is in contact with said tip position of said reference pin.

10. The boring instrument guiding device according to claim 1, wherein said step portion includes a surface transverse to the longitudinal direction of said reference pin.

* * * * *